United States Patent [19]

Hall et al.

[11] 4,119,783
[45] Oct. 10, 1978

[54] 3'LOWER ALKYLCARBONYL OXANILIC ACID ESTERS

[75] Inventors: Charles M. Hall; John B. Wright, both of Kalamazoo, Mich.

[73] Assignee: The Upjohn Company, Kalamazoo, Mich.

[21] Appl. No.: 769,874

[22] Filed: Feb. 18, 1977

[51] Int. Cl.$^2$ .................. C07C 101/44; A61K 31/195
[52] U.S. Cl. .................................. 560/43; 260/465 D; 260/293.75; 260/293.8; 260/326.8; 424/304; 424/309; 424/316; 424/319; 562/436; 562/437; 562/441; 544/109; 562/456; 562/433
[58] Field of Search .................. 260/471 R, 471 A, 43

[56] References Cited

U.S. PATENT DOCUMENTS

| 3,966,965 | 6/1976 | Sellstedt et al. | 560/43 |
| 3,972,911 | 8/1976 | Wright | 260/471 R X |

OTHER PUBLICATIONS

Baker et al., J. Org. Chem. 27, 3283-3289 (1962).
Reichhold, "Chem. Absts" vol. 78, 44448 (s), 1973.

Primary Examiner—James O. Thomas, Jr.
Assistant Examiner—G. T. Breitenstein
Attorney, Agent, or Firm—Martin B. Barancik

[57] ABSTRACT

Pharmaceutical compositions having as the active agent a compound of the formula

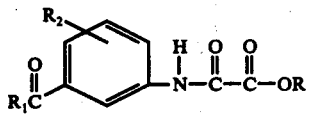

useful for preventing allergic manifestations in sensitized mammals and novel compounds.

4 Claims, No Drawings

3'LOWER ALKYLCARBONYL OXANILIC ACID ESTERS

BRIEF SUMMARY OF THE INVENTION

It has now been discovered that novel compositions of Formula 1 are useful in the prophylactic treatment of sensitized humans and animals for allergy and anaphylactic reactions of a reagin or non-reagin mediated nature. The compounds are formulated with pharmaceutical carriers for oral, parenteral or inhalation means of administration. Certain novel compounds are claimed as well.

DETAILED DESCRIPTION OF THE INVENTION

In accordance with this invention, there are provided pharmaceutical compositions, hereafter referred to as Group A, having an anti-allergy effective amount of a compound of the formula

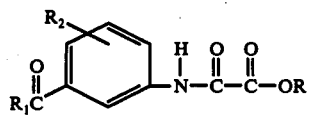

Formula 1 wherein R is hydrogen, a physiologically acceptable metal or amine cation, alkyl of one to eight carbon atoms, inclusive, cycloalkyl of five to six carbon atoms, inclusive, $(CH_2)_n$-phenyl wherein $n$ is 0, 1 or 2, or

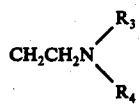

wherein $R_3$ and $R_4$ are the same or different and are alkyl of one to four carbon atoms, inclusive; $R_1$ is alkyl of one to five carbon atoms, inclusive, cycloalkyl of five to six carbon atoms, inclusive, or phenyl; $R_2$ is hydrogen, fluoro, chloro, bromo, trifluoromethyl, nitro, cyano or amino; and physiologically acceptable acid addition salts thereof in association with a pharmaceutical carrier.

A further group of compositions, hereafter referred to as Group B, are those compositions of Group A wherein R is hydrogen, a physiologically acceptable metal or amine cation, cycloalkyl of five to six carbon atoms, inclusive, and alkyl of one to eight carbon atoms, inclusive.

Another group of compositions, hereafter referred to as Group C, are the compositions of Group B wherein $R_1$ is alkyl of one to five carbon atoms, inclusive, and $R_2$ is hydrogen, fluoro, chloro, trifluoromethyl, cyano and amino.

Another group of compositions, hereafter referred to as Group D, are the compositions of Group C wherein R is hydrogen.

A further group of compositions, hereafter referred to as Group E, are the compositions of Group C wherein R is a physiologically acceptable metal or amine cation.

A still further group of compositions, hereafter referred to as Group F, are the compositions of Group C wherein R is alkyl of one to eight carbon atoms, inclusive.

Another group of compositions are those of Groups D, E and F taken singularly wherein $R_1$ is alkyl of one to three carbon atoms, inclusive and $R_2$ is hydrogen.

A further aspect of the invention is a method of preventing allergic manifestations of a reagin or non-reagin mediated nature, particularly asthma, allergic rhinitis, urticaria, food allergy or anaphylactoid reactions comprising the administration of a compound of Formula 1 in association with a pharmaceutical carrier to a mammal in need of said treatment. Allergy of a reagin mediated nature is preferably treated.

Novel compounds of the invention wherein $R_1$ is alkyl of one to three carbon atoms, $R_2$ is hydrogen and R is alkyl of four to eight carbon atoms, inclusive or $(CH_2)_n$-phenyl wherein $n$ is one or two are a further aspect of the invention. Preferred compounds are those compounds wherein R is n-butyl or phenethyl and $R_1$ is methyl.

As employed in the above disclosure and throughout the specification and claims, the phrase "alkyl of one to eight carbon atoms, inclusive" means methyl, ethyl, propyl, butyl, pentyl, hexyl, heptyl, octyl and isomers thereof. Illustrative examples of isomers are isopropyl, tert-butyl, neopentyl, 2,2-dimethylbutyl, 2-methylhexyl and 2,2,4-trimethylpentyl.

Carbon atom limitations of a lower number are to be construed in the same manner.

The phrase "physiologically acceptable amine salt" refers to amines which are accepted by mammals in an essentially non-toxic manner when administered to mammals in conjunction with the acid moiety of the invention. Illustrative of the amines are those derived from primary, secondary or tertiary amines. Examples of suitable amines are methylamine, dimethylamine, triethylamine, ethylamine, dibutylamine, diisopropylamine, N-methylhexylamine, decylamine, dodecylamine, allylamine, crotylamine, cyclopentylamine, dicyclohexylamine, benzylamine, dibenzylamine, α-phenylethylamine, β-phenylethylamine, ethylenediamine, diethylenetriamine, adamantylamines, and like aliphatic, cycloaliphatic, and araliphatic amines containing up to and including about eighteen carbon atoms as well as heterocyclic amines, e.g., piperidine, morpholine, pyrrolidine, piperazine, and lower-alkyl derivatives thereof, e.g., 1-methylpiperidine, 4-ethylmorpholine, 1-isopropylpyrrolidine, 2-methylpyrrolidine, 1,4-dimethylpiperazine, 2-methylpiperidine, and the like, as well as amines containing water-solubilizing or hydrophilic groups, e.g., mono-, di-, and triethanolamine, ethyldiethanolamine, N-butylethanolamine, 2-amino-1-butanol, 2-amino-1-ethyl-1,3-propanediol, 2-amino-2-methyl-1-propanol, tris(hydroxymethyl)aminomethane, N-phenylethanolamine, N-(p-tert-amylphenyl)-diethanolamine, galactamine, N-methylglucamine, N-methylglucosamine, ephedrine, phenylephrine, epinephrine, procaine, and the like.

The term "physiologically acceptable metal" includes alkali metals such as sodium and potassium, alkaline earth metals such as calcium and magnesium and other acceptable metals such as aluminum.

The term "physiologically acceptable acid addition salt thereof" refers to acids which are accepted by mammals in an essentially non-toxic manner when administered to mammals in conjunction with a basic moiety of the invention. For example, acid addition salts of the compounds can be formed when R is

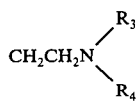

and/or when $R_2$ is amino. Examples of acids which can be utilized are hydrochloric, sulfuric, nitric, lauric, cyclohexanesulfamic and the like.

The compounds of the invention are readily prepared by methods well known in the art. An appropriately $R_2$ substituted m-amino phenone is reacted with an oxalyl halide, preferably ethyl oxalyl chloride, in a suitable solvent and base to form the oxamate. An alternative method of preparing the oxamate is to react the amino compound with an oxalate, preferably diethyl oxalate, in neat solution or with an additional solvent if necessary.

When using an alkyl oxalyl halide, reaction is carried out in base and solvent at standard conditions. Examples of suitable solvents are dimethylformamide, dioxane, and tetrahydrofuran. Appropriate bases include triethylamine, N-methylmorpholine, dimethylpiperazine, and N-methylpiperidine. When the dialkyl oxalate is employed, the amino starting material is heated together with the dialkyl oxalate or an additional solvent such as a xylene or diphenyl ether if desired, thereby forming the oxamate. The temperature is from about 25° C. to the reflux temperature of the system.

At this point of the synthetic pathway, the oxamate can be transesterified to other esters and/or converted to the acid by hydrolysis and thence to the metal or amine salts by standard methods.

The oxamate is readily converted to the oxamic acid by using dilute base such as sodium hydroxide, potassium hydroxide or potassium carbonate at temperatures ranging from about 25° to about 100° C., followed by addition of acid.

Following are illustrative examples of the invention.

Table I

| R | $R_1$ | $R_2$ |
|---|---|---|
| $CH_3$ | $C_6H_{11}$ | H |
| $C_2H_5$ | $i\text{-}C_3H_7$ | 4-F |
| $C_3H_7$ | $C_2H_5$ | 5-Cl |
| $i\text{-}C_3H_7$ | $i\text{-}C_4H_9$ | 6-Br |
| $n\text{-}C_4H_9$ | $C_5H_9$ | $2\text{-}NO_2$ |
| $i\text{-}C_4H_9$ | $C_6H_5$ | $4\text{-}NH_2$ |
| $t\text{-}C_4H_9$ | $C_2H_5$ | $5\text{-}CF_3$ |
| $n\text{-}C_5H_{11}$ | $n\text{-}C_5H_{11}$ | $6\text{-}NH_2$ |
| $i\text{-}C_5H_{11}$ | $CH_3$ | 6-Cl |
| neopentyl | $C_3H_7$ | H |
| $n\text{-}C_6H_{13}$ | $C_6H_5$ | 2-Br |
| 2-methylpentyl | $C_6H_{11}$ | 2-F |
| 2,3-dimethylbutyl | $C_4H_9$ | $6\text{-}NO_2$ |
| $n\text{-}C_7H_{15}$ | $C_5H_9$ | $5\text{-}NH_2$ |
| 2-methylhexyl | $C_2H_5$ | H |
| $C_2H_5$ | $CH_3$ | 5-CN |
| $n\text{-}C_8H_{17}$ | $CH_3$ | H |
| 2-methylheptyl | $i\text{-}C_5H_{11}$ | 4-F |
| 2,2,4-trimethylpentyl | $t\text{-}C_4H_9$ | 6-Cl |
| $C_6H_5$ | $C_6H_5$ | 2-Br |
| $CH_2C_6H_5$ | $n\text{-}C_5H_{11}$ | $6\text{-}CF_3$ |
| $CH_2CH_2C_6H_5$ | $n\text{-}C_4H_9$ | $6\text{-}NO_2$ |
| $\underset{\mid}{CH_3}$<br>$CH-C_6H_5$ | $i\text{-}C_3H_7$ | $5\text{-}NH_2$ |

Table I-continued

| R | $R_1$ | $R_2$ |
|---|---|---|
| $CH_2CH_2N\begin{array}{l}CH_3\\CH_3\end{array}$ | $n\text{-}C_3H_7$ | 4-Br |
| $CH_2CH_2N\begin{array}{l}C_2H_5\\C_3H_7\end{array}$ | $C_2H_5$ | 2-Cl |
| $CH_2CH_2N\begin{array}{l}CH_3\\i\text{-}C_3H_7\end{array}$ | $CH_3$ | H |

Table II

The esters of Table I are converted to the acid, R is hydrogen, by conventional means. Thereafter the acid can be converted to the physiologically acceptable metal or amine cation, such as sodium, potassium and tris(hydroxymethyl)methylammonium and the like by standard methods.

Following are additional examples of compounds of the invention and compounds which can be compounded into compositions of the invention which are useful for the methods of the invention. All temperatures are in degrees centigrade.

EXAMPLE 1 Ethyl 3'-acetyloxanilate

A solution of 18.92 g. (0.14 mole) of m-aminoacetophenone in 200 ml. of ethyl acetate with 18.22 g. (0.18 mole) of triethylamine is cooled to 5° in an ice-bath. To the solution is added 24.6 g. (0.18 mole) of ethyloxalyl chloride. The mixture is stirred for 1 hour in the ice-bath. The reaction mixture is allowed to warm to room temperature overnight.

The precipitate is removed by filtration and the filtrate evaporated to a solid residue in vacuo. The residue is recrystallized from ethanol. There is obtained 21.2 g. (64%) of white needles that melt at 104°–106°. Additional recrystallization raises the melting point to 105°–6°.

EXAMPLE 2 Butyl 3'-acetyloxanilate

A mixture of m-aminoacetophenone (5.0 g., 0.0370 mole), butyl oxalyl chloride (6.0 g., 0.0365 mole), triethylamine (4.0 g., 0.0395 mole) and anhydrous dimethylformamide (50 ml.) is stirred at room temperature for 20 hours. The reaction mixture is poured into water and the resulting yellow solid collected. Recrystallization from benzene-Skellysolve B gives a yellow solid (4.29 g., melting point 102°, 44%).

Analysis Found: C, 64.10; H, 6.77; N, 5.29.

EXAMPLE 3 Phenethyl 3'-acetyloxanilate

A mixture of m-aminoacetophenone (5.0 g., 0.0370 mole), anhydrous dimethylformamide (50 ml.), triethylamine (4.5 g., 0.0395 mole) and phenethyl oxalyl chloride (8.0 g., 0.0376 mole) is stirred at room temperature for 20 hours. The reaction mixture is poured into water and the resulting solid collected. Recrystallization from benzene-Skellysolve B gives a yellow solid (4.51 g., melting point 88°, 39%).

Analysis Found: C, 69.30; H, 5.63; N, 4.39.

The compositions of the present invention are presented for administration to humans and animals in unit dosage forms, such as tablets, capsules, pills, powders, granules, sterile parenteral solutions or suspensions, eye drops, oral solutions or suspensions, and oil-in-water and water-in-oil emulsions containing suitable quantities of the compound of Formula 1. The preferred method of administration is orally utilizing an ester of the active compound.

For oral administration, either solid or fluid unit dosage forms can be prepared. For preparing solid compositions such as tablets, the compound of Formula 1 is mixed with conventional ingredients such as talc, magnesium stearate, dicalcium phosphate, magnesium aluminum silicate, calcium sulfate, starch, lactose, acacia, methylcellulose, and functionally similar materials as pharmaceutical diluents or carriers. Capsules are prepared by mixing the compound with an inert pharmaceutical diluent and filling the mixture into a hard gelatin capsule of appropriate size. Soft gelatin capsules are prepared by machine encapsulation of a slurry of the compound with an acceptable vegetable oil, light liquid petrolatum or other inert oil.

Fluid unit dosage forms for oral administration such as syrups, elixirs, and suspensions can be prepared. The water-soluble forms can be dissolved in an aqueous vehicle together with sugar, aromatic flavoring agents and preservatives to form a syrup. An elixir is prepared by using a hydroalcoholic (ethanol) vehicle with suitable sweeteners such as sugar and saccharin, together with an aromatic flavoring agent.

Suspensions can be prepared with an aqueous vehicle with the aid of a suspending agent such as acacia, tragacanth, methylcellulose and the like.

For parenteral administration, fluid unit dosage forms are prepared utilizing the compound and a sterile vehicle, water being preferred. The compound, depending on the vehicle and concentration used, can be either suspended or dissolved in the vehicle. In preparing solutions the compound can be dissolved in water for injection and filter sterilized before filling into a suitable vial or ampoule and sealing. Advantageously, adjuvants such as a local anesthetic, preservative and buffering agents can be dissolved in the vehicle. To enhance the stability, the composition can be frozen after filling into the vial and the water removed under vacuum. The dry lyophilized powder is then sealed in the vial and an accompanying vial of water for injection is supplied to reconstitute the liquid prior to use. Parenteral suspensions can be prepared in substantially the same manner except that the compound is suspended in the vehicle instead of being dissolved and sterilization cannot be accomplished by filtration. The compound can be sterilized by exposure to ethylene oxide before suspending in the sterile vehicle. Advantageously, a surfactant or wetting agent is included in the composition to facilitate uniform distribution of the compound.

The preferred compositions are those adapted for oral administration.

For treatment of allergic conditions of the nose, such as rhinitis, compositions adapted for contact with nasal linings are preferred.

Compositions for inhalation are of three basic types: (1) a powder mixture preferably micropulverized with particle size preferably from about 1 to about 5 microns; (2) an aqueous solution to be sprayed with a nebulizer; and (3) an aerosol with volatile propellant in a pressurized container.

The powders are quite simply prepared by mixing a compound of the formula with a solid base which is compatible with lung tissue, preferably lactose. The powders are packaged in a device adapted to emit a measured amount of powder when inhaled through the mouth.

Aqueous solutions are prepared by dissolving the compound of the Formula 1 in water and adding salt to provide an isotonic solution and buffering to a pH compatible with inhalation. The solutions are dispersed in a spray device or nebulizer and sprayed into the mouth while inhaling.

Aerosols are prepared by dissolving a compound of the Formula 1 in water or ethanol and mixing with a volatile propellant and placing in a pressurized container having a metering valve to release a predetermined amount of material.

The liquefied propellant employed is one which has a boiling point below 65° F. at atmospheric pressure. For use in compositions intended to produce aerosols for medicinal use, the liquefied propellant should be non-toxic. Among the suitable liquefied propellants which may be employed are the lower alkanes containing up to five carbon atoms, such as butane and pentane, or a lower alkyl chloride, such as methyl, ethyl, or propyl chlorides. Further suitable liquefied propellants are the fluorinated and fluorochlorinated lower alkanes such as are sold under the trademarks "Freon" and "Genetron." Mixtures of the above-mintioned propellants may suitably be employed. Examples of these propellants are dichlorodifluoromethane ("Freon 12"), dichlorotetrafluoroethane ("Freon 114"), trichloromonofluoromethane ("Freon 11"), dichloromonofluoromethane ("Freon 21"), monochlorodifluoromethane ("Freon 22"), trichlorotrifluoroethane ("Freon 113"), difluoroethane ("Genetron 142-A") and monochlorotrifluoromethane ("Freon 13").

The term "unit dosage form," as used in the specification and claims, refers to physically discrete units suitable as unitary dosages for human subjects and animals, each unit containing a predetermined quantity of active material calculated to produce the desired therapeutic diluent, carrier or vehicle. The specifications for the novel unit dosage forms of this invention are dictated by and directly dependent on (a) the unique characteristics of the active material and the particular effect to be achieved and (b) the limitations inherent in the art of compounding such an active material for use in humans and animals, as disclosed in detail in this specification, these being features of the present invention. Examples of suitable unit dosage forms in accord with this invention are tablets, capsules, pills, coated tablets, powder packets, wafers, granules, cachets, teaspoonfuls, tablespoonfuls, dropperfuls, ampoules, vials, aerosols with metered discharges, segregated multiples of any of the foregoing, and other forms as herein described.

Those delivery systems with solid pharmaceutical carriers can be used as an appropriate vehicle. Liquid pharmaceutical carriers can also be used as an appropriate vehicle. These liquid vehicles are separated into aqueous and non-aqueous systems. Oral unit dosage forms which are preferred are tablets, capsules, pills, and powders. Liquid carriers can be divided into a unit dosage by the potential recipient of the drug, for example, droppersful, teaspoonsful, tablespoonsful, and unit dosages of other magnitude.

An effective but non-toxic quantity of the compound is employed in treatment. The dosage of the compound for treatment depends on the route of administration and the potency of the particular compound. A dosage schedule for humans of from about 0.05 to about 10 mg. of compound in a single dose, administered parenterally or by inhalation in the compositions of this invention are effective for preventing allergy attacks. More specifically, the single dose is from about 0.5 to about 5 mg. of compound. The oral dose is from about 0.5 to about 30 mg. in a single dose. More specifically, the single dose is from about 1 to about 20 mg. of compound. The dosage to be administered can be repeated up to four times daily. However, when it is necessary to repeat treatment, a preferred dosage schedule reduces the secondary treatment dosage to from about 0.5 percent to about 20 percent of the above dosages, more specifically, from about 1 to about 10 percent of the above dosages. In this manner, a state of allergy prophylaxis can be maintained. The reduced dosage is taken until that dosage no longer provides effective protection. At that time, the larger dosage is repeated, followed by the reduced dosage. An example of such a dosage schedule is the following: An asthmatic individual swallows 10 mg. of n-butyl-3'-acetyloxanilate. Four hours later, the individual swallows 2 mg. of the same compound and every four to six hours thereafter swallows 2 mg. of the same compound until effective asthma prophylaxis is not provided. The individual then swallows 10 mg. of the same compound and reduces the oral dosage to 2 mg. four to six hours later. The dosage schedule continues in this manner.

The administration of the compositions of the present invention to humans and animals provides a method for the prophylactic treatment of allergy and anaphylactoid reactions of a reagin or non-reagin, preferably reagin, mediated nature. That is to say, these compositions, when administered to a sensitized individual prior to the time that the individual comes into contact with substances (antigens) to which he is allergic, will prevent the allergic reaction which would otherwise occur. Treatment of allergy of a reagin mediated nature is preferred.

For example, the process can be used for treatment of such conditions as bronchial asthma, allergic rhinitis, food allergy, urticaria, exercise or stress induced asthma, anaphylactoid reactions and bird fancier's disease. Preferred conditions for treatment are bronchial asthma, allergic rhinitis, food allergy and urticaria. More preferred conditions are bronchial asthma and allergic rhinitis.

EXAMPLE 4

A lot of 10,000 tablets, each containing 10 mg. of n-butyl 3'-acetyloxanilate is prepared from the following types and amounts of ingredients:
n-Butyl 3'-acetyloxanilate — 100 Gm.
Dicalcium phosphate — 1,000 Gm.
Methylcellulose, U.S.P.(15 cps) — 60 Gm.
Talc — 150 Gm.
Corn starch — 200 Gm.
Magnesium stearate — 10 Gm.

The compound and dicalcium phosphate are mixed well, granulated with 7.5 percent solution of methylcellulose in water, passed through a No. 8 screen and dried carefully. The dried granules are passed through a No. 12 screen, mixed thoroughly with the talc, starch and magnesium stearate, and compressed into tablets.

These tablets are useful in preventing hay fever attacks at a dose of one tablet every four to six hours.

EXAMPLE 5

One thousand two-piece hard gelatin capsules, each containing 5 mg. of n-butyl 3'-acetyloxanilate, are prepared from the following types and amounts of ingredients:
n-Butyl 3'-acetyloxanilate — 5 Gm.
Talc — 50 Gm.
Lactose — 100 Gm.
Magnesium stearate — 1 Gm.

The ingredients are mixed well and filled into capsules of the proper size.

Capsules so prepared are useful in preventing attacks of bronchial asthma at a dose of one capsule every four to six hours.

EXAMPLE 6

One thousand tablets, each containing 10 mg. of n-butyl 3'-acetyloxanilate, are prepared from the following types and amounts of ingredients:
n-Butyl 3'-acetyloxanilate — 10 Gm.
Microcrystalline cellulose NF — 410 Gm.
Starch — 100 Gm.
Magnesium stearate powder — 3 Gm.

The ingredients are screened and blended together and pressed into tablets.

The tablets are useful to protect against food allergy at a dose of one tablet before meals.

EXAMPLE 7

One thousand tablets, each containing 20 mg. of n-butyl 3'-acetyloxanilate, are prepared from the following types and amounts of ingredients:
n-Butyl 3'-acetyloxanilate — 20 Gm.
Microcrystalline cellulose NF — 410 Gm.
Starch — 100 Gm.
Magnesium stearate powder — 3 Gm.

The ingredients are screened and blended together and pressed into tablets.

The tablets are useful to protect against urticaria at a dose of one tablet every four to six hours.

EXAMPLE 8

A sterile preparation suitable for intramuscular injection and containing 2 mg. of 3'-acetyloxanilic acid in each milliliter is prepared from the following ingredients:
3'-Acetyloxanilic acid — 2 Gm.
Methylparaben — 1.5 Gm.
Propylparaben — 0.5 Gm.
Cottonseed oil q.s. — 1,000 ml.

One milliliter of this sterile preparation is injected for prophylactic treatment of allergic rhinitis.

EXAMPLE 9

Six hundred ml. of an aqueous solution containing 5.0 mg. of the tris(hydroxymethyl)aminomethane salt of 3'-acetyloxanilic acid per ml. is prepared as follows:
Tris(hydroxymethyl)aminomethane salt of 3'-acetyloxanilic acid — 3 Gm.
Sodium chloride — 5 Gm.
Water for injection q.s. — 600 ml.

The THAM salt and sodium chloride are dissolved in sufficient water to make 600 ml. and sterile filtered.

The solution is placed in nebulizers designed to deliver 0.25 ml. of solution per spray.

One spray of the solution is inhaled into the lungs every four to six hours for prevention of asthmatic attacks.

EXAMPLE 10

A powder mixture consisting of 0.5 grams of sodio 3'-acetyloxanilate and sufficient lactose to make five grams of mixture is micropulverized and placed in an insufflator designed to deliver 50 mg. of powder per dose.

A single dose of the powder is inhaled into the lungs every four to six hours for prevention of asthmatic attacks.

A single dose of the powder is inhaled intranasally every four to six hours for prevention of rhinitis.

EXAMPLE 11

Twelve grams of an aerosol composition are prepared from the following ingredients:
Tris(hydroxymethyl)aminomethane salt of 3'-acetyloxanilic acid — 1.00 Gm.
Freon 12 — 1.44 Gm.
Freon 114 — 2.16 Gm.
Water — 6.80 Gm.
Sorbitan monoleate — 0.60 Gm.

The THAM salt is dissolved in the water and added to the Freons. The twelve grams of compositions are added to a 13 cc plastic coated bottle and capped with a metering valve. The metering valve releases 80 mg. of composition in an aerosol. Eighty milligrams of the aerosol is inhaled every four to six hours for prevention of asthmatic attacks.

EXAMPLE 12

In individuals who require continual treatment in the Examples 4 through 11, the dosage of the Example is given initially and each succeeding administration of the drug is at 1/50 of the initial dosage. This maintenance dosage is continued until effective allergy prophylaxis is not obtained. The initial dosage of Example 4 through 11 is then started once more, followed by the maintenance dosages.

EXAMPLE 13

After allowing for the different solubilities of the compounds and the activity of the particular compound as measured, for example, by the in vivo rat passive cutaneous anaphylaxis assay, a suitable quantity of each of the compounds, assuming appropriate solubility, of Examples 1, 3 and Tables I and II is substituted for the active compound in the compositions and uses of Examples 4 through 11. Results showing anti-allergy activity are obtained.

EXAMPLE 14

The rat passive cutaneous anaphylaxis assay is run in the following manner:

Female Sprague-Dawley 250 gm. rats are skin-sensitized with rat anti-ovalbumin homocytotropic anti-body that is heat labile and has a passive cutaneous anaphylaxis titer of 1:128. After a 72-hour latency period, the animals are challenged i.v. with 4 mg. ovalbumin (OA) + 5 mg. Evans blue dye and the test compound. If the test compound is administered orally, a solution or suspension of the test compound in 0.5% methylcellulose in water is administered at an appropriate time interval before challenge. Thirty minutes later, the extravascular bluing that results from antigen antibody combination at the skin site is read. Antibody dilutions are used such that in control animals a 4 mm spot is the lowest detectable spot, and 4 or 5 lower dilutions are used to give a range of antibody in each animal. Four to five animals are used for each variable in the experiment. Percent inhibition of the PCA assay is calculated by comparing the spot scores of treated rats with the spot scores of control rats. The spot score is the total number of detectable spots divided by the number of animals.

N-Butyl 3'-acetyloxanilate administered orally two hours before antigen challenge provided effective inhibition in the rat passive cutaneous anaphylaxis assay.

Certain of the higher esters, particularly the n-butyl and phenethyl 3'-acetyloxanilate, have longer duration of activity and can be administered after longer intervals, for example, every six to ten hours.

We claim:

1. A compound of the formula

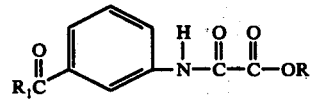

wherein $R_1$ is alkyl of one to three carbon atoms, inclusive, and R is alkyl of four to eight carbon atoms, inclusive, or $(CH_2)_n$-phenyl wherein $n$ is one or two.

2. A compound in accordance with claim 1 wherein $R_1$ is methyl.

3. n-Butyl 3'-acetyloxanilate according to claim 1.

4. Phenethyl 3'-acetyloxanilate according to claim 1.

* * * * *